(12) United States Patent
Kang et al.

(10) Patent No.: US 10,078,211 B2
(45) Date of Patent: Sep. 18, 2018

(54) APPARATUS FOR TRANSFERRING IMAGE DATA AND ENDOSCOPY SYSTEM INCLUDING THE SAME

(71) Applicant: INTHESMART Inc., Seoul (KR)

(72) Inventors: Uk Kang, Seoul (KR); Ilhyung Shin, Jeju (KR)

(73) Assignee: INTHESMART INC., Seoul (KR)

( * ) Notice: Subject to any disclaimer, the term of this patent is extended or adjusted under 35 U.S.C. 154(b) by 129 days.

(21) Appl. No.: 15/201,475

(22) Filed: Jul. 3, 2016

(65) Prior Publication Data

US 2017/0184837 A1   Jun. 29, 2017

(30) Foreign Application Priority Data

Dec. 29, 2015  (KR) .................. 10-2015-0188070
Mar. 14, 2016  (KR) .................. 10-2016-0030050

(51) Int. Cl.
| | | |
|---|---|---|
| *G02B 23/24* | (2006.01) | |
| *H04N 5/225* | (2006.01) | |
| *A61B 1/00* | (2006.01) | |
| *H04N 5/232* | (2006.01) | |

(52) U.S. Cl.
CPC ............ *G02B 23/2484* (2013.01); *A61B 1/00* (2013.01); *H04N 5/2253* (2013.01); *H04N 5/232* (2013.01); *H04N 2005/2255* (2013.01)

(58) Field of Classification Search
None
See application file for complete search history.

(56) References Cited

U.S. PATENT DOCUMENTS

| | | | | |
|---|---|---|---|---|
| 5,609,561 A | * | 3/1997 | Uehara ................. | A61B 1/042 348/75 |
| 2010/0274090 A1 | * | 10/2010 | Ozaki ................ | A61B 1/00096 600/173 |
| 2012/0016202 A1 | * | 1/2012 | Baum ................ | A61B 1/00114 600/182 |

FOREIGN PATENT DOCUMENTS

| | | |
|---|---|---|
| CN | 103705201 A | 4/2014 |
| KR | 10-1021891 B1 | 3/2011 |
| KR | 101021891 B1 * | 3/2011 |

\* cited by examiner

*Primary Examiner* — James M Anderson, II
(74) *Attorney, Agent, or Firm* — Patent Office of Dr. Chung Park

(57) ABSTRACT

An endoscope system according to the present disclosure includes an apparatus for transferring image data configured to include an image sensor which generates image data and which includes a first image terminal and a second image terminal for transferring at least a portion of the image data, and to include a first optical fiber module and a second optical fiber module which are connected with the first image terminal and the second image terminal respectively; an image data input unit configured to be connected with the apparatus for transferring image data and to transfer the image data output through the apparatus for transferring image data via a set path; and an image processing unit configured to perform an image processing for the image data transferred from the image data input unit under control of CPU.

30 Claims, 13 Drawing Sheets

[Fig. 1]
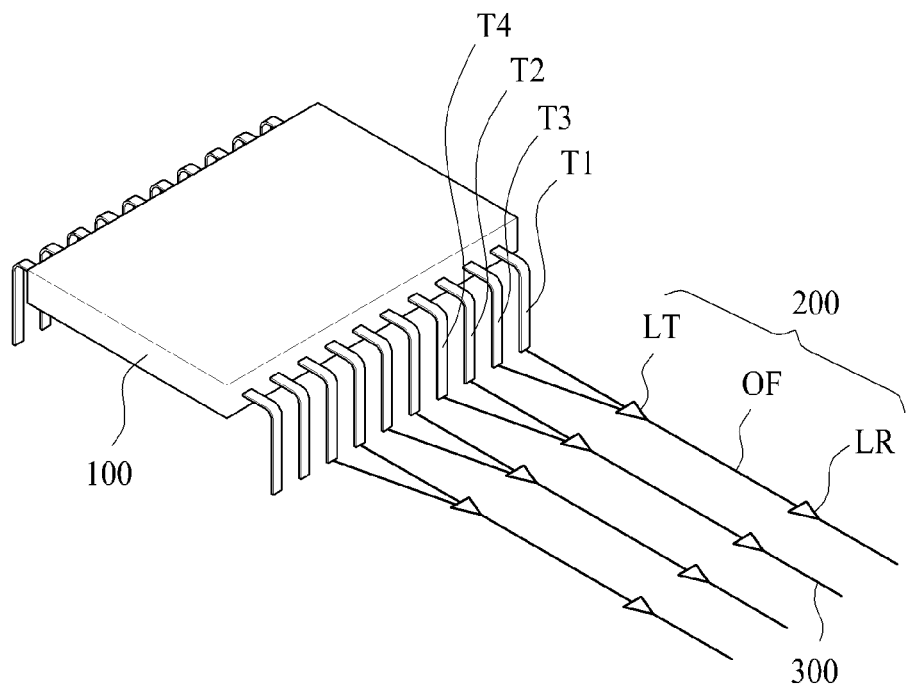

[Fig. 2]
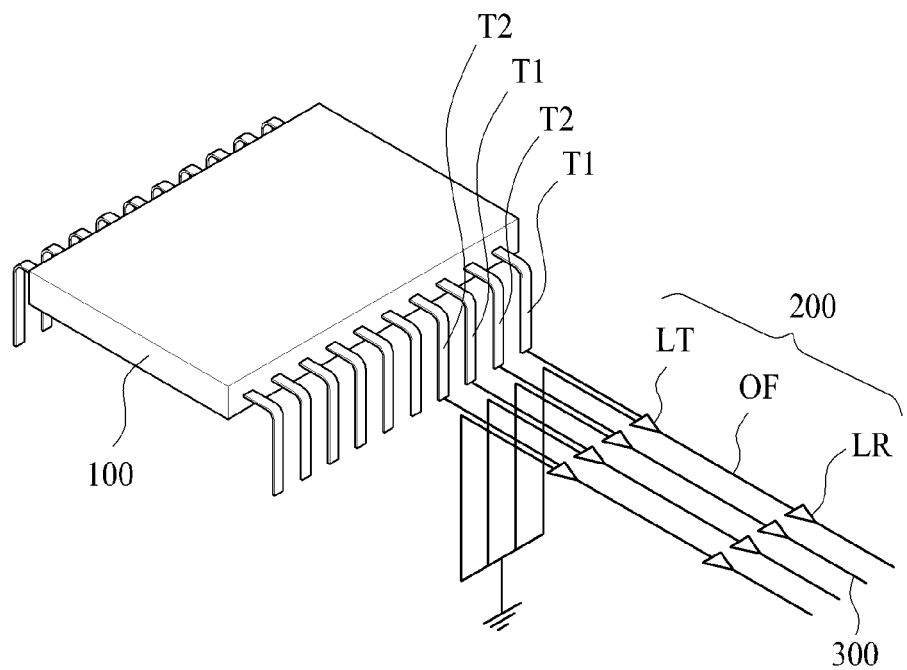

[Fig. 3]
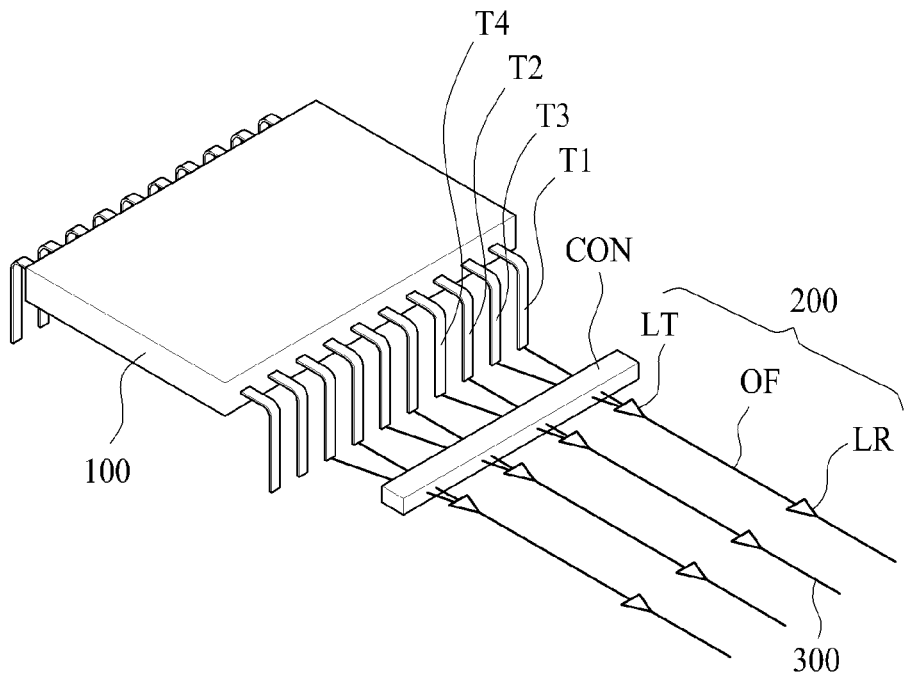
[Fig. 4]
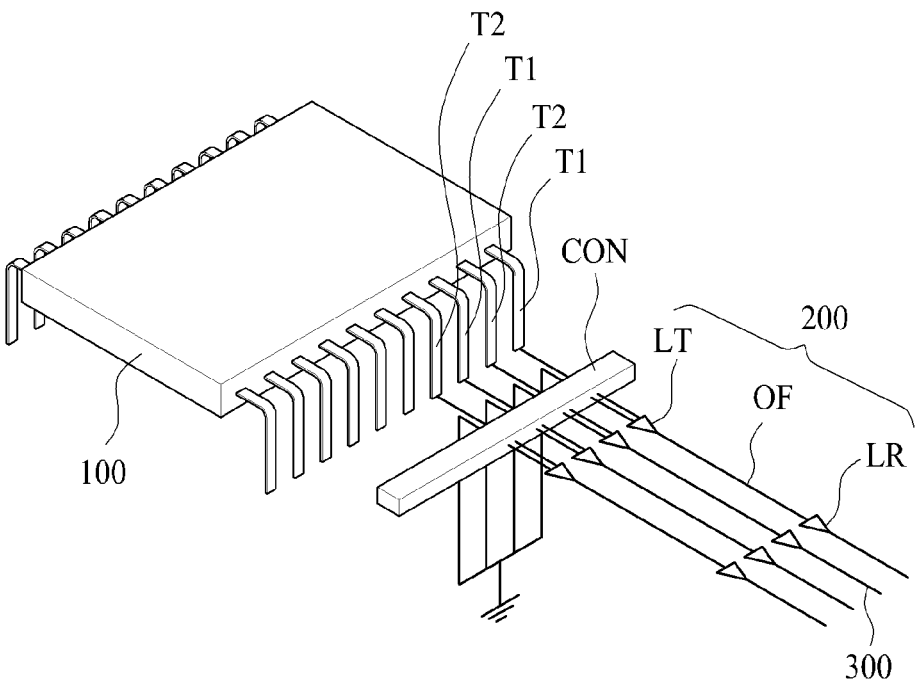

[Fig. 5]
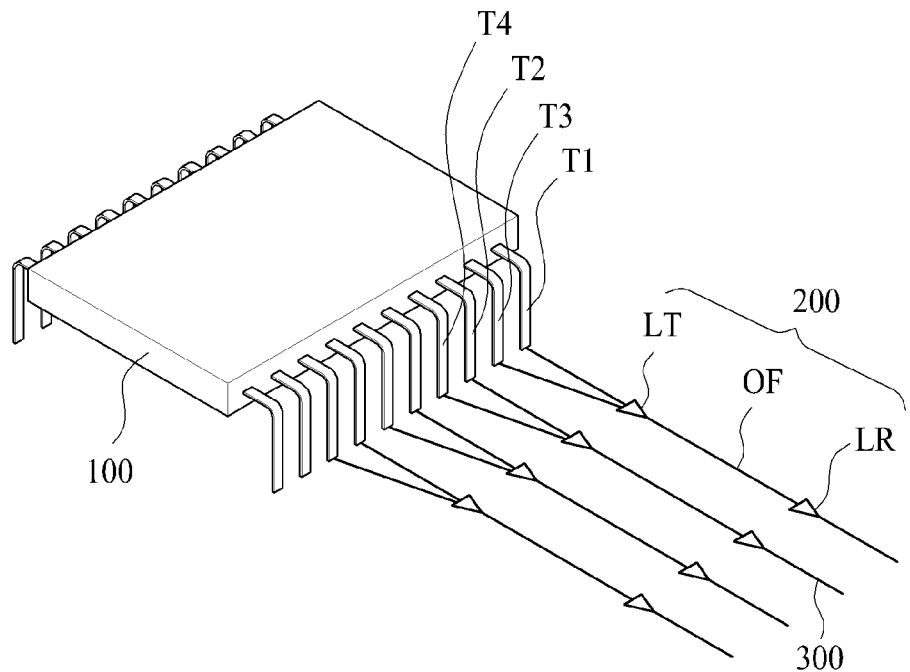
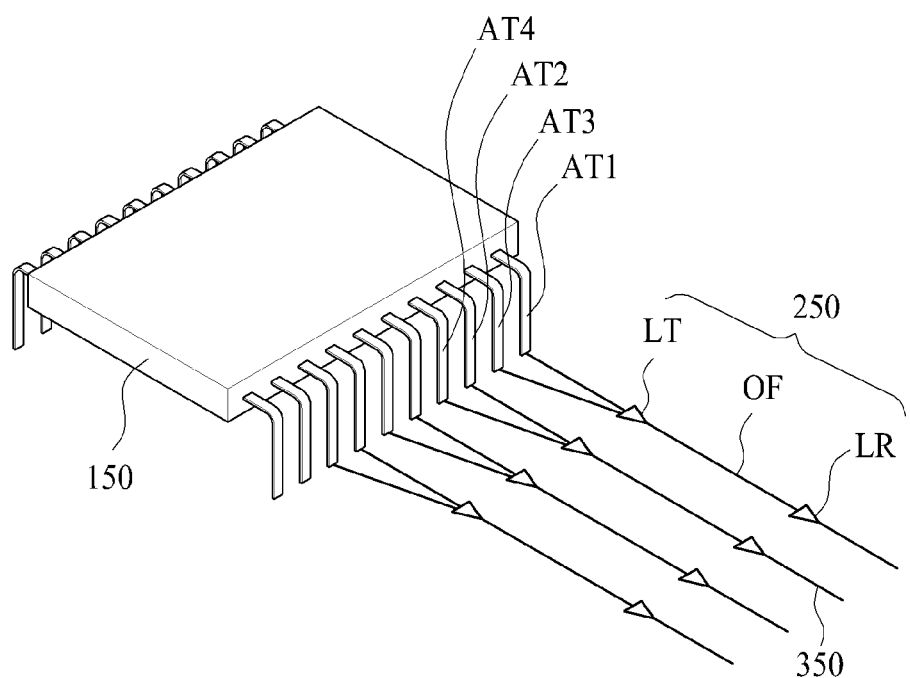

[Fig. 6]
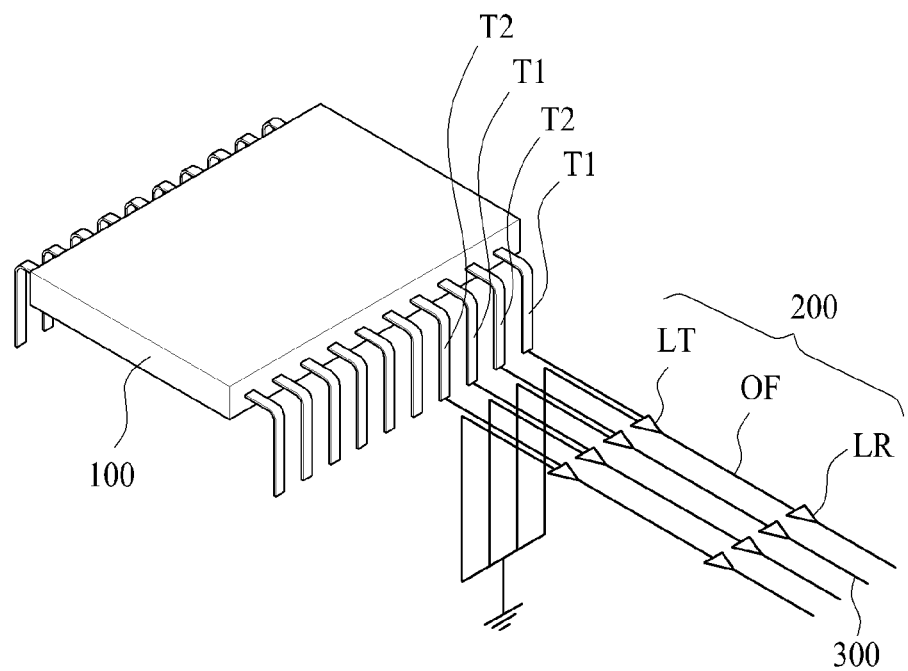
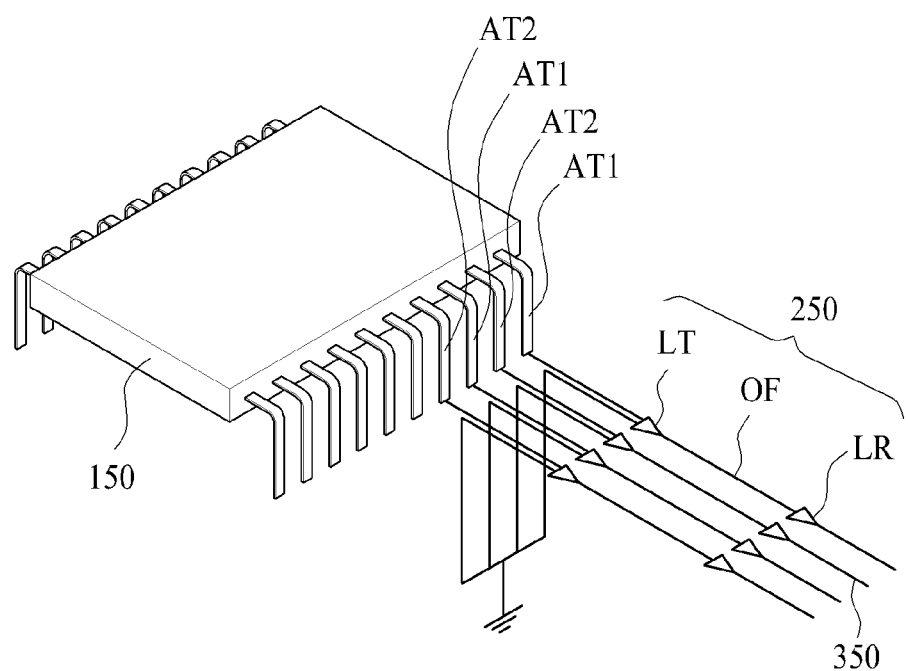

[Fig. 7]
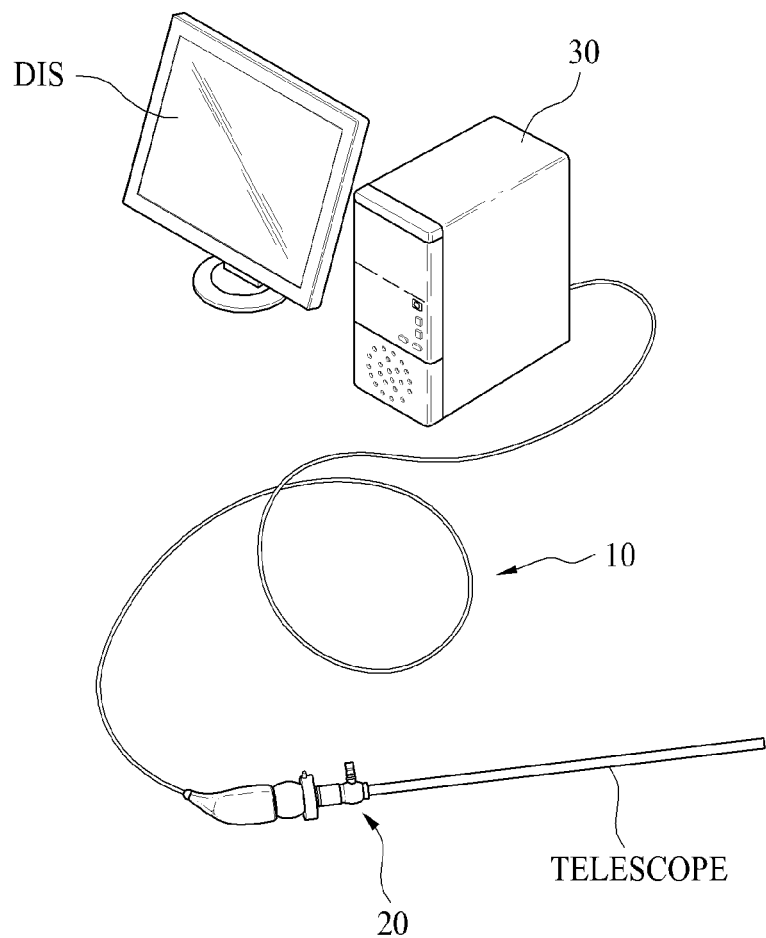

[Fig. 8]
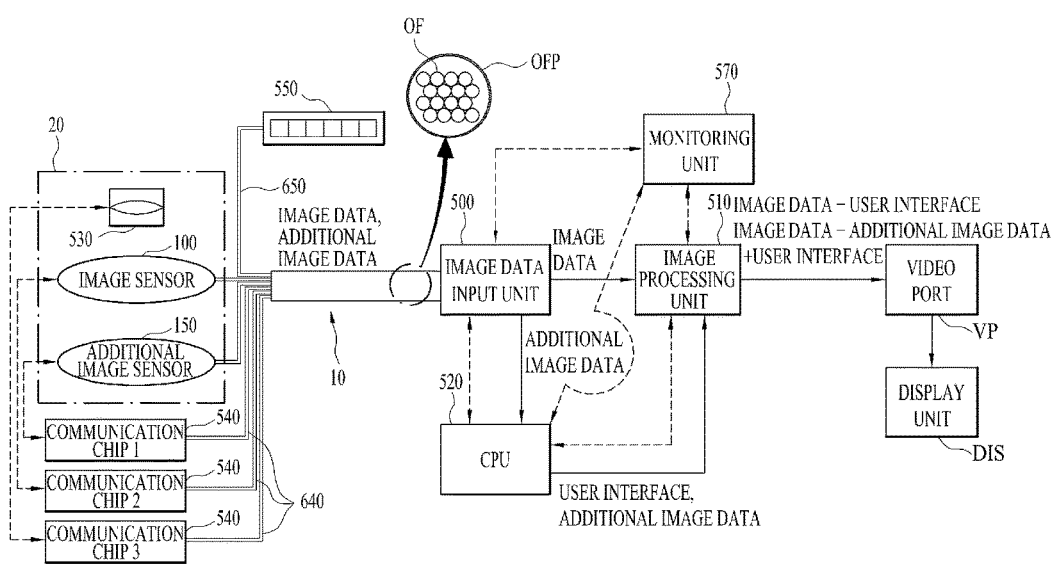

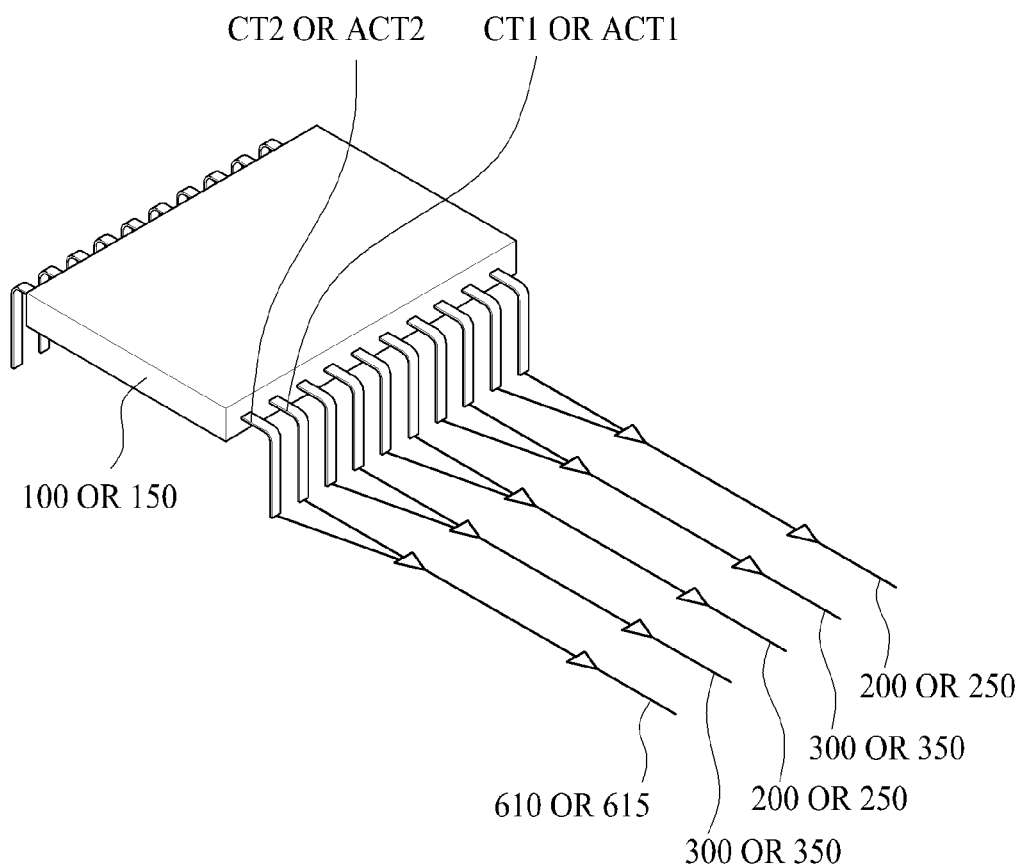
[Fig. 9]

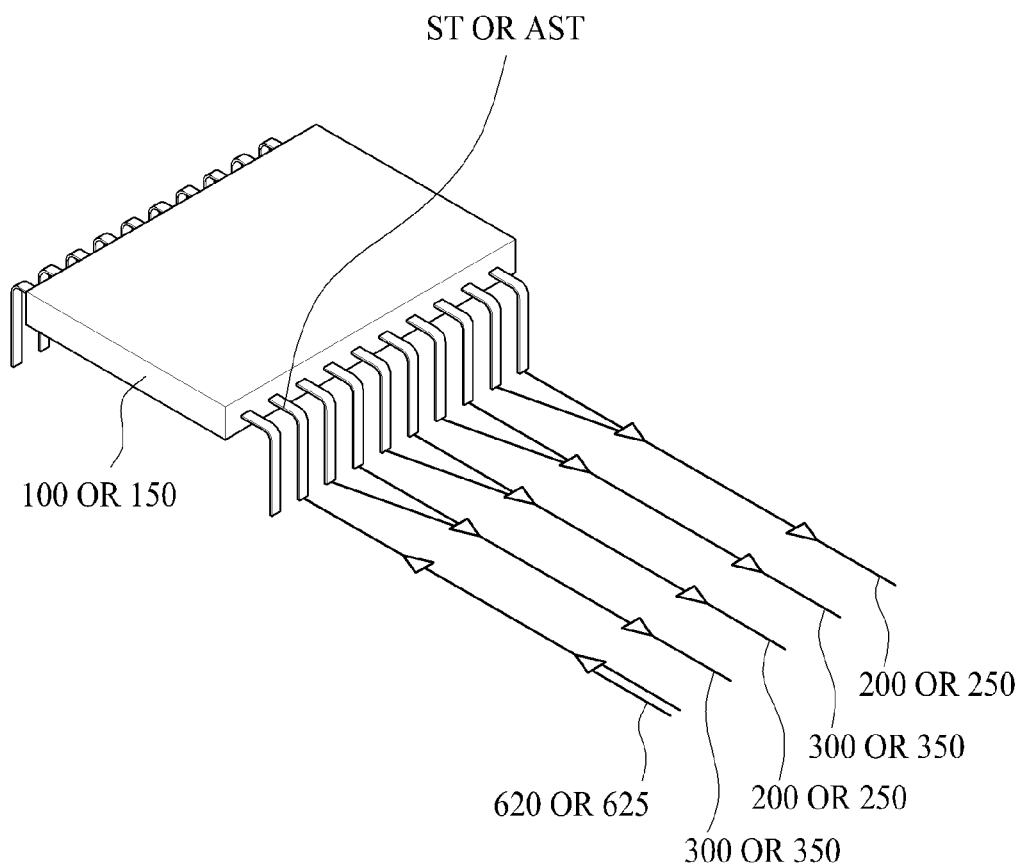
[Fig. 10]

[Fig. 11]
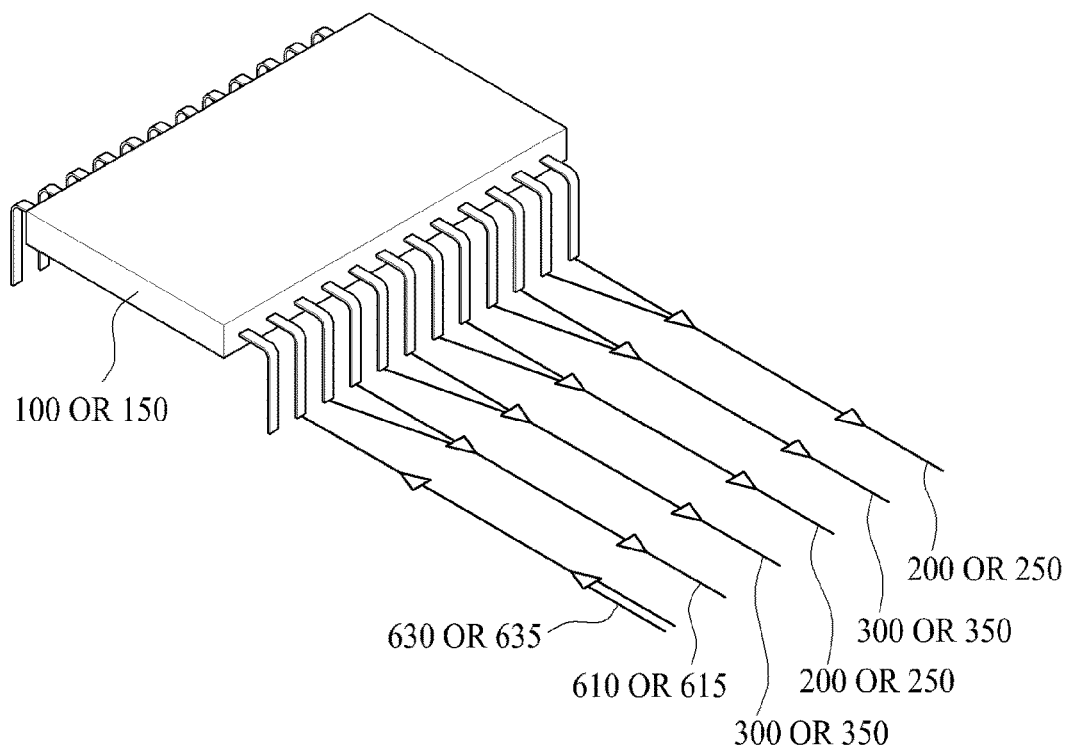
< IN THE CASE OF MIPI CSI II>

[Fig. 12]
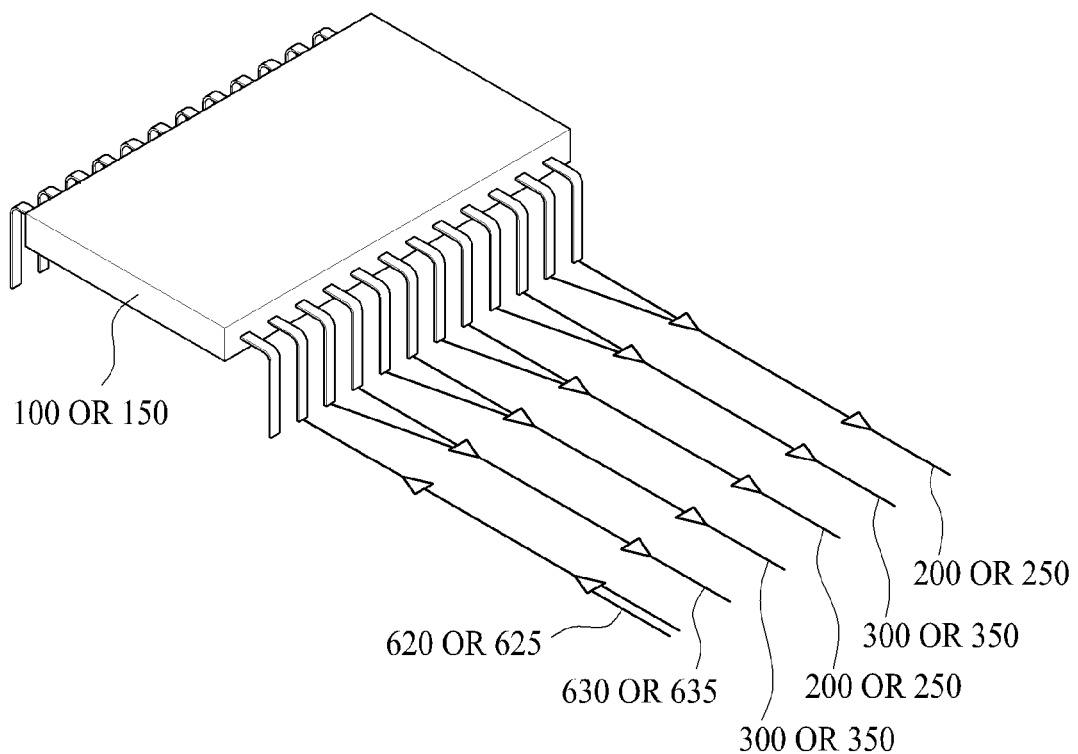
< IN THE CASE OF MIPI CSI III >

[Fig. 13]
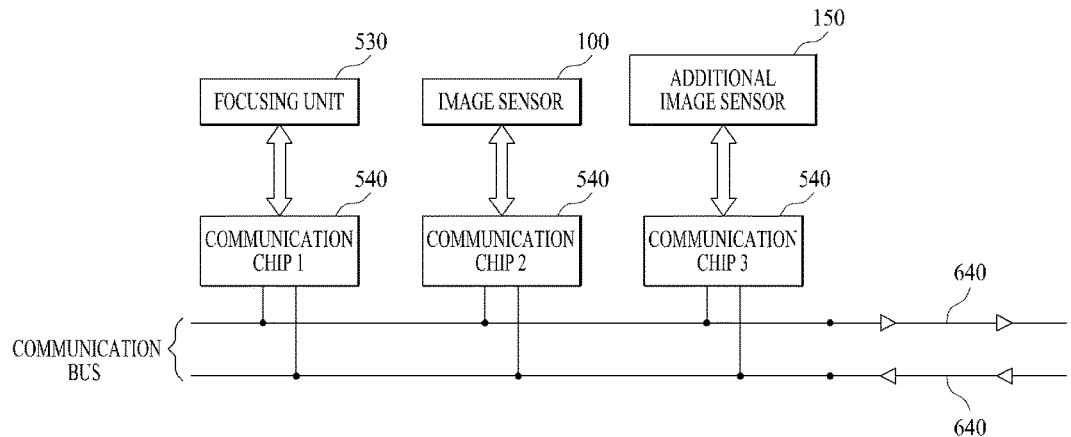
[Fig. 14]
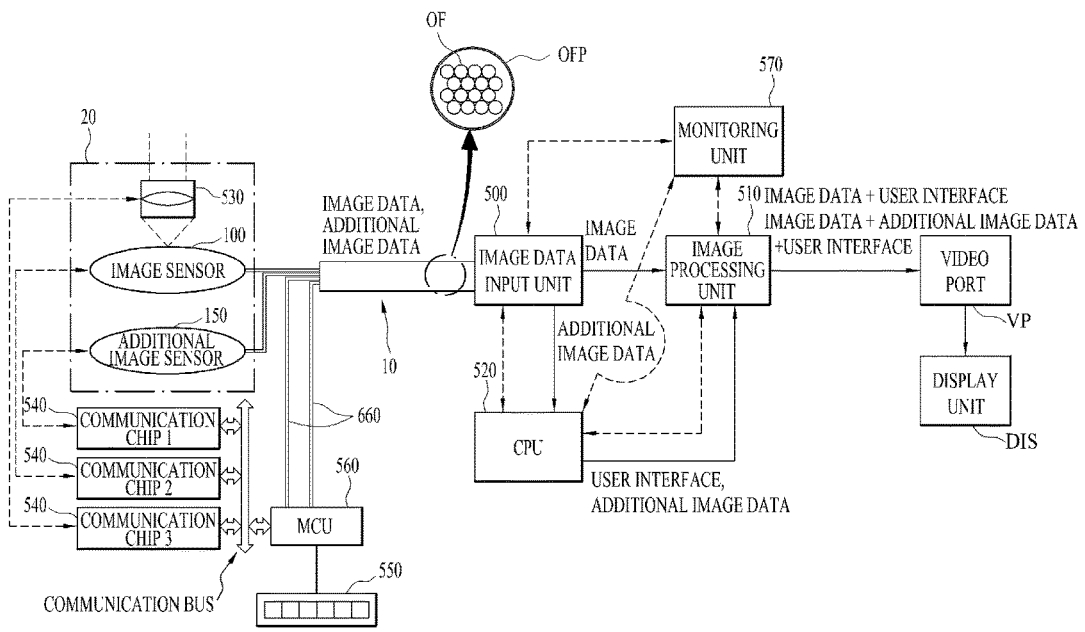

[Fig. 15]
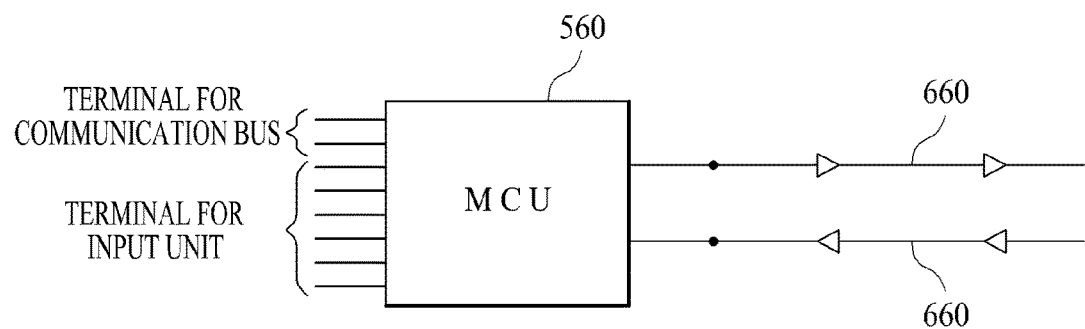

APPARATUS FOR TRANSFERRING IMAGE DATA AND ENDOSCOPY SYSTEM INCLUDING THE SAME

CROSS-REFERENCE TO RELATED APPLICATIONS

This application claims priority under 35 U.S.C. § 119 from Korean Application No. 10-2015-0188070 filed on Dec. 29, 2015 and Korean Application No. 10-2016-0030050 filed on Mar. 14, 2016, the subject matter of which is incorporated herein by reference.

BACKGROUND OF THE INVENTION

Field of the Invention

The present disclosure relates to an apparatus for transferring image data and an endoscopy system including the same.

Description of the Related Art

Since an endoscopy system provides a doctor with an image of the inner body in a surgery or checkup procedure and the doctor can check the image, it is possible to accurately and reliably accomplish the surgery or the checkup procedure.

Recently, the endoscopy system is increasingly required to provide various functions as well as just images.

Accordingly, a research on an endoscopy system that can provide various functions while performing a high speed image processing is progressed.

SUMMARY OF THE INVENTION

The present disclosure has been made in view of the above problems, and provides an apparatus for transferring image data and an endoscopy system including the same capable of overcoming a limitation of bandwidth during the transferring of the image data.

In accordance with an aspect of the present disclosure, an apparatus for transferring image data includes: an image sensor configured to generate an image data, and to comprise a first image terminal and a second image terminal for transferring at least a portion of the image data; and a first optical fiber module and a second optical fiber module connected to the first image terminal and the second image terminal respectively.

The first optical fiber module is connected to a third image terminal together with the first image terminal, the second optical fiber module is connected to a fourth image terminal together with the second image terminal, and the first optical fiber module and the second optical fiber module transfer the image data in a differential mode.

The first optical fiber module and the second optical fiber module transfer the image data in a single-ended mode.

At least a portion of the image data is transferred through the first optical fiber module and the second optical fiber module without a serialization process for the image data.

The first optical fiber module and the second optical fiber module are directly connected to the first image terminal and the second image terminal, or connected to the first image terminal and the second image terminal through a connector.

The apparatus further includes an additional image sensor configured to generate an additional image data by sensing a light having a wavelength different from a wavelength of light sensed by the image sensor, and to include a first additional image terminal and a second additional terminal for transferring at least a portion of the additional image data, and a first additional optical fiber module and a second additional optical fiber module which are connected to the first additional image terminal and the second additional terminal respectively.

The first additional optical fiber module is connected to a third additional image terminal together with the first additional image terminal, the second additional optical fiber module is connected with a fourth additional image terminal together with the second additional image terminal, and the first additional optical fiber module and the second additional optical fiber module transfer the additional image data in a differential mode.

The first additional optical fiber module and the second additional optical fiber module transfer the additional image data in a single-ended mode.

At least a portion of the additional image data is transferred through the first additional optical fiber module and the second additional optical fiber module without a serialization process for the additional image data.

In accordance with another aspect of the present disclosure, an endoscope system includes: an apparatus for transferring image data configured to include an image sensor which generates image data and which includes a first image terminal and a second image terminal for transferring at least a portion of the image data, and to include a first optical fiber module and a second optical fiber module which are connected with the first image terminal and the second image terminal respectively; an image data input unit configured to be connected with the apparatus for transferring image data and to transfer the image data output through the apparatus for transferring image data via a set path; and an image processing unit configured to perform an image processing for the image data transferred from the image data input unit under control of CPU.

The CPU processes an user interface for the image data, and the image processing unit overlaps the user interface with the image data.

The first optical fiber module and the second optical fiber module transfer the image data in a differential mode or a single-ended mode.

At least a portion of the image data is transferred through the first optical fiber module and the second optical fiber module without a serialization process for the image data.

The first optical fiber module and the second optical fiber module are directly connected to the first image terminal and the second image terminal, or connected to the first image terminal and the second image terminal through a connector.

The endoscope system in accordance with another aspect of the present disclosure further includes an additional image sensor configured to generate an additional image data by sensing a light having a wavelength different from a wavelength of light sensed by the image sensor, and to include a first additional image terminal and a second additional terminal for transferring at least a portion of the additional image data, and a first additional optical fiber module and a second additional optical fiber module which are connected to the first additional image terminal and the second additional terminal respectively to transfer the additional image data in a differential mode or single-ended mode.

The image data input unit receives the additional image data together with the image data and transfers the additional image data to the CPU, and transfers the image data to the image processing unit, and the image processing unit receives the additional image data from the CPU to overlap with the image data.

The image sensor further includes a first clock terminal, and the apparatus for transferring image data further includes a clock optical fiber module connected with the first clock terminal, wherein the clock optical fiber module transfers a clock signal in a differential-mode or a single-ended mode.

A transfer direction of the image data which the first optical fiber module and the second optical fiber module transfer is identical with a transfer direction of the clock signal which the clock optical fiber module transfers.

The apparatus for transferring image data further includes a dummy optical fiber module which is able to transfer a signal in an opposite direction of the transfer direction of the image data and the clock signal.

The additional image sensor further includes a first additional clock terminal, and the apparatus for transferring image data further includes a clock additional optical fiber module connected to the first additional clock terminal, wherein the clock additional optical fiber module transfers a clock signal in the differential-mode or the single-ended mode.

Transfer directions of the additional image data and the clock signal of the first additional optical fiber module, the second additional optical fiber module, and the clock additional optical fiber module are identical.

The endoscope system in accordance with another aspect of the present disclosure further includes an additional dummy optical fiber module which is able to transfer a signal in the opposite direction of the transfer direction of the additional image data and the clock signal.

The apparatus for transferring image data further includes a synchronization confirmation optical fiber module, wherein the synchronization confirmation optical fiber module transfers a synchronization confirmation signal in the differential-mode or the single-ended mode.

The transfer direction of the image data of the first optical fiber module and the second optical fiber module is opposite to the transfer direction of the synchronization confirmation signal of the synchronization confirmation optical fiber module.

The endoscope system in accordance with another aspect of the present disclosure further includes a dummy optical fiber module configured to transfer a signal in the same direction as the transfer direction of the image data.

When one of the first optical fiber module and the second optical fiber module is an abnormal optical fiber module which is not able to transfer the image data, the dummy optical fiber module transfers the image data instead of the abnormal optical fiber module.

The apparatus for transferring image data further includes a synchronization confirmation additional optical fiber module, wherein synchronization confirmation additional optical fiber module transfers a synchronization confirmation signal in the differential mode or the single-ended mode.

The transfer direction of the additional image data of the first additional optical fiber module and the second additional optical fiber module is opposite to the transfer direction of the synchronization confirmation signal of the synchronization confirmation additional optical fiber module.

The endoscope system in accordance with another aspect of the present disclosure further includes an additional dummy optical fiber module configured to transfer a signal in the same direction as the transfer direction of the additional image data.

When one of the first additional optical fiber module and the second additional optical fiber module is an abnormal additional optical fiber module which is not able to transfer the image data, the additional dummy optical fiber module transfers the image data instead of the abnormal additional optical fiber module.

The endoscope system in accordance with another aspect of the present disclosure further includes an input unit which is able to be handled by a user, a MCU configured to encode an input signal of the input unit, and a third optical fiber module configured to be connected to the MCU and to transfer the input signal encoded by the MCU, and the number of the third optical fiber module for transferring the encoded input signal is smaller than the number of input pins of the MCU for receiving the input signal from the input unit.

The endoscope system in accordance with another aspect of the present disclosure further includes: an additional image sensor configured to generate additional image data by sensing a light having a wavelength different from a wavelength of light sensed by the image sensor; a MCU configured to input and output a control signal and operation information for the image sensor and the additional image sensor; and a third optical fiber module configured to be connected to the MCU to transfer and receive the control signal and the operation information to and from the CPU; wherein the number of the third optical fiber module is smaller than or equal to the number of pins of the MCU for inputting and outputting the control signal and the operation information.

The apparatus for transferring image data further includes a protection unit configured to protect each optical fiber of the first optical fiber module and the second optical fiber module, wherein the protection unit is implemented of material that is able to withstand autoclave for disinfection of a medical device.

The endoscope system in accordance with another aspect of the present disclosure further includes a monitoring unit configured to monitor at least one of the image data input unit, the CPU, and the image processing unit in real time to perform a reset of the at least one according to a state value of the at least one.

The image sensor and the CPU communicate via a communication bus, wherein the communication bus comprises a transfer bus line and a receive bus line, and the transfer bus line and the receive bus line are connected with a control optical fiber module respectively.

BRIEF DESCRIPTION OF THE DRAWINGS

The objects, features and advantages of the present disclosure will be more apparent from the following detailed description in conjunction with the accompanying drawings, in which:

FIG. 1 to FIG. 6 are diagrams illustrating an apparatus for transferring image data according to an embodiment of the present disclosure;

FIG. 7 is a diagram illustrating an example of a configuration of an endoscope system according to an embodiment of the present disclosure;

FIG. 8 is a block diagram illustrating an endoscope system according to an embodiment of the present disclosure;

FIG. 9 to FIG. 12 are diagrams illustrating various modifications of an apparatus for transferring image data of an endoscopic system according to an embodiment of the present disclosure;

FIG. 13 is a diagram illustrating an example of a communications chip and a control optical fiber module of an endoscope system according to an embodiment of the present disclosure;

FIG. 14 is a block diagram illustrating an endoscope system according to an embodiment of the present disclosure; and FIG. 15 is a diagram illustrating an example of MCU and a third optical fiber module of an endoscope system according to an embodiment of the present disclosure.

DETAILED DESCRIPTION OF EXEMPLARY EMBODIMENTS

Exemplary embodiments of the present disclosure are described with reference to the accompanying drawings in detail. The same reference numbers are used throughout the drawings to refer to the same or like parts. Detailed descriptions of well-known functions and structures incorporated herein may be omitted to avoid obscuring the subject matter of the present disclosure.

The terms and words used in the following description and claims are not limited to the bibliographical meanings, but, are merely used by the inventor to enable a clear and consistent understanding of the present disclosure. It is to be understood that the singular forms "a," "an," and "the" include plural referents unless the context clearly dictates otherwise.

In the present disclosure, the terms such as "include" and/or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

Hereinafter, an apparatus for transferring image data and an endoscopic system according to an embodiment of the present disclosure are described with reference to the accompanying drawings.

FIG. 1 and FIG. 2 are a diagram illustrating an apparatus for transferring image data according to an embodiment of the present disclosure. As shown in FIG. 1 and FIG. 2, the apparatus for transferring image data according to an embodiment of the present disclosure may include an image sensor 100, a first optical fiber module 200, and a second optical fiber module 300.

The image sensor 100 may generate image data, and includes a first image terminal T1 and a second image terminal T2 for transferring the image data. The image sensor 100 may generate image data generated according to a standard which can be processed in an application processor (AP) which is a CPU for mobile device.

For example, the image sensor 100 may generate image data of a mobile industry processor interface (MIPI) standard, a low-voltage differential signaling (LVDS) standard, a parallel interface standard and the like, but it is not limited thereto. The MIPI standard may be used to transfer the image data at a high speed in a mobile device such as a smart phone.

The first optical fiber module 200 and the second optical fiber module 300 may be connected with the first image terminal T1 and the second image terminal T2 respectively. In FIGS. 1 and 2, and in FIGS. 3 to 6 which are described later, the number of the first image terminal T1 and the second image terminal T2 may be changed according to a transfer standard of the image data.

As shown in FIG. 1 and FIG. 2, the first optical fiber module 200 and the second optical fiber module 300 may include a light emitting unit LT, an optical fiber OF, and a light reception unit LR. The light emitting unit LT may convert an electrical signal into an optical signal, and the optical fiber OF may transfer the converted optical signal, and the light reception unit LR may convert again the optical signal transferred through the optical fiber OF into an electrical signal.

In addition to the first optical fiber module 200 and the second optical fiber module 300, various optical fiber modules which are described later may also include the light emitting unit LT, the optical fiber OF, and the light reception unit LR.

As shown in FIG. 1 and FIG. 2, a single optical fiber module may be connected to a single image terminal of the image sensor 100. Accordingly, the apparatus for transferring image data according to an embodiment of the present disclosure may have various advantages in comparison with the method of transferring image data via a coaxial cable.

Dissimilarly to the embodiment of the present disclosure, when the entire image terminals of the image sensor 100 are connected to a single coaxial cable to transfer image data, a serializer and a deserializer may be required.

The serializer may serialize the image data outputted from a plurality of image terminal through switching and transfer to a single coaxial cable, and the deserializer may recover the serialized image data transferred via the coaxial cable to its original state through switching.

Accordingly, the bandwidth of the serializer and the deserializer should be larger than the result of multiplying the bandwidth of the image terminal with the number of image terminal. In this case, the serializer and the deserializer may be overloaded.

That is, since the bandwidth of the serializer and the deserializer is large, clocks may be accelerated to increase power consumption, and thus a lot of heat may be generated in the serializer and the deserializer. When the heat generation is increased, the life of the serializer and the deserializer may be shortened and the operational reliability may be decreased.

In addition, since it takes time for the serializer and the deserializer to process image data, the transfer time of the image data may be increased. For example, when a doctor performs surgery while determining the inner body of patient through an endoscope system, a video containing the surgery act of the doctor should be displayed in real time.

When the transfer time of the image data is increased through the serializer and the deserializer, the video display may be delayed, so that the doctor may check his/her own surgery act after a certain period of time is elapsed and an unexpected medical malpractice may occur.

In particular, when the amount of image data to be processed is large, for example, when the image data to be processed is a full HD quality (hereafter, FHD quality) or a ultra HD quality (hereafter, UHD quality), the operation burden of the serializer and the deserializer may also be increased.

Meanwhile, since the coaxial cable is connected to the serializer and the deserializer, the bandwidth of coaxial cable also should be broad. The maximum bandwidth of the coaxial cable may be 10 Gbps, and 12.5 Gbps bandwidth of the transfer line may be required to transfer the UHD-quality video at 60 frames per second. Accordingly, there may be a limit to transfer a high-resolution video through the coaxial cable.

Therefore, if the image data of high resolution is transferred through the coaxial cable, the image data may be compressed by an encoder and may be transferred to the serializer, and a decoder may restore the compressed image data which passed through the deserializer to its original state.

Accordingly, a transfer delay of the image data according to the encoder and the decoder, a heat generation, a complexity of configuration, and the like may occur. Furthermore, an electromagnetic wave may be increased due to the image data of high speed transferred through the coaxial cable, and thus, the possibility of the distortion of the image data or the generation of noise may be increased.

Alternatively, similarly to the embodiment of the present disclosure, when a single image terminal is connected to a single optical fiber module, the image data may be transferred through the optical fiber module without the previously described serializer and deserializer. Accordingly, the heat generation, the complex configuration, the operation reliability degradation, and the like due to the serializer, the deserializer, the encoder, the decoder, and the like may be solved.

As described above, since a single image terminal is connected to a single optical fiber module, the limitation of bandwidth of coaxial cable that occurs when the FHD-quality image data or the UHD-quality image data is transferred may be overcome.

That is, the apparatus for transferring image data according to an embodiment of the present disclosure may transfer at least a portion of the image data through the first optical fiber module and the second optical fiber module without a serialization process for the image data.

Meanwhile, as shown in FIG. 1, the first optical fiber module 200 may be connected with a third image terminal T3 together with the first image terminal T1, and the second optical fiber module 300 may be connected with a fourth image terminal T4 together with the second image terminal T2. In this case, the first optical fiber module 200 and the second optical fiber module 300 may transfer the image data in a differential mode.

That is, the first optical fiber module 200 may transfer the image data according to a voltage difference between the first image terminal T1 and the third image terminal T3, and the second optical fiber module 300 may also transfer the image data according to a voltage difference between the second image terminal T2 and the fourth image terminal T4.

For example, when the light emitting unit LT includes a vertical cavity surface emitting laser (VCSEL), an input of the VCSEL may include two terminals (terminal P and terminal N). In this case, the VCSEL may perform the differential mode. That is, when a voltage difference is generated between two terminals, light is emitted, whereas when the voltage difference does not exist, light may not be emitted.

The light reception unit LR may include an optical transistor, and a voltage may generated between source and drain when the optical transistor receives light. The light reception unit LR may amplify this voltage to form a differential voltage of a desired magnitude.

In addition, as shown in FIG. 2, the first optical fiber module and the second optical fiber module may transfer the image data in a single-ended mode. For example, the terminal P of each VCSEL may be connected to the first image terminal T1 or the second image terminal T2, and the terminal N of each VCSEL may be connected to ground.

When a voltage difference is generated between the terminal N and the terminal P, the VCSEL may emit light, so that it is possible to convert the image data input from the terminal P into an optical signal even if the terminal N is connected to ground.

Meanwhile, as shown in FIG. 1 and FIG. 2, the first optical fiber module 200 and the second optical fiber module 300 may be directly connected to the first image terminal T1 and the second image terminal T2. Alternatively, as shown in FIG. 3 and FIG. 4, the first optical fiber module 200 and the second optical fiber module 300 may be connected to the first image terminal T1 and the second image terminal T2 through a connector (CON).

The apparatus for transferring image data according to an embodiment of the present disclosure may further include an additional image sensor 150, a first additional optical fiber module 250, and a second additional optical fiber module 350. The additional image sensor 150 may generate an additional image data by sensing a light having a wavelength different from the wavelength of light sensed by the image sensor 100, and may include a first additional image terminal AT1 and a second additional terminal AT2 for transferring at least a portion of the additional image data.

In this case, the first additional optical fiber module 250 and the second additional optical fiber module 350 may be connected to the first additional image terminal AT1 and the second additional terminal AT2 respectively.

For example, the image sensor 100 may sense a visible light, and the additional image sensor 150 may sense infrared rays or ultraviolet rays, but it is not limited thereto. The additional image sensor 150 is described later in more detail.

Meanwhile, as shown in FIG. 5, the first additional optical fiber module 250 may be connected to a third additional terminal AT3 together with the first additional image terminal AT1.

In addition, the second additional optical fiber module 350 may be connected to a fourth additional terminal AT4 together with the second additional image terminal AT2.

In this case, the first additional optical fiber module 250 and the second additional optical fiber module 350 may transfer the additional image data in a differential mode.

Accordingly, the first additional optical fiber module 250 may transfer the additional image data according to a voltage difference between the first additional image terminal AT1 and the third additional image terminal AT3. In addition, the second additional optical fiber module 350 may also transfer the image data according to a voltage difference between the second additional image terminal AT2 and the fourth additional image terminal AT4.

Meanwhile, as shown in FIG. 6, the first additional optical fiber module 250 and the second additional optical fiber module 350 may transfer the additional image data through a single-ended mode. That is, the light emitting unit LT of the first additional optical fiber module 250 and the second additional optical fiber module 350 may have two terminals, and one of two terminals may be connected to ground. Thus, when a voltage difference between two terminals is generated, the light emitting unit LT may emit a light in accordance with the voltage difference.

As described above, at least a portion of the additional image data may be transferred via the first additional optical fiber module 250 and the second additional optical fiber module 350 without the serialization process for the additional image data.

Next, the endoscope system according to an embodiment of the present disclosure is described with reference to drawings.

FIG. 7 and FIG. 8 are a diagram illustrating an endoscope system according to an embodiment of the present disclosure. FIG. 7 shows an example of a configuration of the endoscope system according to an embodiment of the present disclosure.

The endoscope system according to an embodiment of the present disclosure may include an image generation unit 20 connected to one side of an apparatus for transferring image data 10. The image generation unit 20 may include at least one of the image sensor 100 and the additional image sensor 150. In this case, the apparatus for transferring image data 10 may include a protection unit OFP for covering a plurality of optical fibers OF. The protection unit OFP is described later in detail with reference to FIG. 8.

The image generation unit 20 may be connected to a telescope equipped with a lens array which is provided therein. A body 30 may include at least one constituent element of hardware or software which is connected to the other side of the apparatus for transferring image data 10 to process the image data or the additional image data.

The endoscope system shown in FIG. 7 is just an example of a configuration of the endoscope system according to an embodiment of the present disclosure, but is not limited thereto.

As shown in FIG. 8, the endoscope system according to an embodiment of the present disclosure may include the apparatus for transferring image data 10, an image data input unit 500, and an image processing unit 510. In FIG. 8, a dotted line arrow represents a control signal of a CPU 520 for an image data input unit 500, the image processing unit 510, and a monitoring unit 570 which is described later.

The apparatus for transferring image data 10 may include the image sensor 100 which generates image data and which includes the first image terminal T1 and the second image terminal T2 for transferring at least a portion of the image data, and may include the first optical fiber module 200 and the second optical fiber module 300 which are connected with the first image terminal T1 and the second image terminal T2 respectively.

Since the apparatus for transferring image data 10 is described above in detail, an explanation thereof is omitted.

The image data input unit 500 may be connected with the apparatus for transferring image data 10 and may transfer the image data output by the apparatus for transferring image data 10 via a set path. For example, the image data input unit 500 may transfer the image data to the image processing unit 510.

In addition, the image data input unit 500 may perform a simple processing (e.g., contrast adjustment, zoom-in, zoom-out, etc.) for the image data, and such a simple processing may be controlled by the CPU 520.

The image processing unit 510 may perform an image processing for the image data transferred from the image data input unit 500 under the control of the CPU 520.

As explained above, the image sensor 100 may generate the image data generated in accordance with the standard which is able to be processed in the application processor (AP) which is the CPU 520 for mobile device.

Like this, when the image data is based on a signal standard for the mobile device, the CPU 520 may also include a mobile chip such as a ARM core.

Thus, the CPU 520 may support a mobile operating system (OS) such as android OS or iOS, and various functions provided by the mobile OS may be applied to the endoscope system according to an embodiment of the present disclosure.

For example, the endoscope system according to an embodiment of the present disclosure may provide a rich user interface, and it is possible to easily upgrade the function desired by the user such as a doctor.

In the present disclosure, the CPU 520 is not limited to the CPU for mobile device. Accordingly, the CPU 150 may operate in a general OS such as windows series OS or OS X.

In this case, the CPU 520 may output an operation control signal according to the user interface processing for the image data and the user's handling of the user interface. The user interface may include a menu, and may be intended to be used for the operation control of the endoscope system and the handling of the image displayed on a display unit (DIS), but it is not limited thereto.

The handling of the image data through the user interface may be intended to be used for the expansion or the reduction of image, the change in the sharpness or the luminance, and the like, but it is not limited thereto.

At this time, although not shown in the drawing, the CPU 520 may include memory (not shown) for storing data or information for the user interface.

The image processing unit 510 may overlap the user interface with the image data output from the image data input unit 500, and may process the image data according to the operation control signal.

In this case, at least one of the image data input unit 500 and the image processing unit 510 may be implemented as a field-programmable gate array (FPGA), but it is not limited thereto.

The FPGA is a kind of non-memory semiconductor which is able to be programmed, and its circuitry is able to be changed again for a specific purpose, unlike a normal semiconductor whose circuit is not able to be changed. The FPGA may implement a desired circuit through the operation of a switching device which is a hardware element, and thus, the image data may be transferred or processed at a high speed as compared with the transferring or the processing by software.

The image processing unit 510 may transfer the overlapped image data and the user interface to the display unit (DIS) via a video port (VP). The video port (VP) may be a Video Graphics Array (VGA), a Digital Visual Interface (DVI), a High Definition Multimedia Interface (HDMI), or a Low Voltage Differential Signaling (LVDS), a Serial Digital Interface (SDI), but it is not limited thereto.

In the endoscope system according to an embodiment of the present disclosure, the processing path of the user interface may be different from the processing path of the image data. That is, in the case of the endoscope system according to an embodiment of the present disclosure, the CPU 520 may process the user interface, and the image data input unit 500 and the image processing unit 510 may process the image data.

A doctor may perform surgery while viewing the image generated by the endoscope system, and a precise surgery can be performed only when the doctor is able to immediately see the condition of the inner body in a surgical procedure as a video.

When a doctor is not able to immediately see the condition of the inner body as a video in a surgical procedure, even if the doctor makes a mistake, the doctor may not immediately recognize the mistake. Therefore, the endoscopic system should be able to process the image data for the inner body at a high speed to display on the display unit (DIS) such as a monitor.

On the other hand, the processing of the user interface may not have a strong influence on the surgical procedure, even if it is late in comparison with the processing of the image data of the inner body.

Differently from the endoscopic system according to an embodiment of the present disclosure, when the image data and the user interface are processed via a single image processing path, the processing of the image data may also be slowed down due to the processing of the user interface, thus, it may have a bad influence on the surgery.

In the case of the endoscope system according to an embodiment of the present disclosure, the image data input unit 500 and the image processing unit may process the image data at a high speed and the CPU 520 may process the user interface at a relatively low speed so that the image processing unit 510 may overlap the image data and the user interface.

Accordingly, since doctor is able to see the overlapped image data and user interface through the display unit (DIS), the doctor may utilize various functions of the endoscope system through the user interface handling even when the doctor less feel or does not recognize the time delay caused by the processing process of the image data.

In addition, since the endoscope system according to an embodiment of the present disclosure includes the above described apparatus for transferring image data 10, it may transfer the image data of high resolution or ultra high resolution while overcoming the limitations of the bandwidth.

Further, the endoscope system according to an embodiment of the present disclosure may transfer the image data without the encoder, the serializer, the deserializer, or the decoder, so that it is possible to provide a simple structure to reduce a transfer time delay of the image data.

That is, the endoscope system according to an embodiment of the present disclosure may transfer at least a portion of the image data through the first optical fiber module and second optical fiber module without the serialization process for the image data.

Although not shown in FIG. 8, a memory between the CPU 520 and the image processing unit 510 may be provided to process the data for the user interface.

On the other hand, the first optical fiber module 200 may be connected with the third image terminal T3 together with the first image terminal T1, and the second optical fiber module 300 may be connected with the image terminal T4 together with the second image terminal T2. The first optical fiber module 200 and the second optical fiber module 300 may transfer the image data in a differential mode. Since this operation is described above in detail, a description thereof is omitted.

Alternatively, one of the light emitting unit LT terminals of the apparatus for transferring image data 10 may be connected to ground so that the apparatus for transferring image data 10 may transfer the image data in a single-ended mode. Since this operation is described above in detail, a description thereof is omitted.

Meanwhile, the first optical fiber module 200 and the second optical fiber module 300 may be directly connected with the first image terminal T1 and the second image terminal T2, or may be connected with the first image terminal T1 and the second image terminal T2 through a connector (CON). Since this operation is described above in detail, a description thereof is omitted.

The apparatus for transferring image data 10 of the endoscope system according to an embodiment of the present disclosure may further include the additional image sensor 150, the first additional optical fiber module 250, and the second additional optical fiber module 350.

The additional image sensor 150 may generate an additional image data by sensing a light having a wavelength different from the wavelength of light sensed by the image sensor 100, and may include a first additional image terminal AT1 and a second additional terminal AT2 for transferring at least a portion of the additional image data.

The first additional optical fiber module 250 and the second additional optical fiber module 350 may be connected to the first additional image terminal AT1 and the second additional terminal AT2 respectively to transfer the additional image data in a differential-mode or a single-ended mode. Since this operation is described above in detail, a description thereof is omitted.

In addition, the image data input unit 500 may receive the additional image data together with the image data and transfer the additional image data to the CPU 520, and transfer the image data to the image processing unit 510. In this case, the image processing unit 510 may receive the additional image data from the CPU 520 to overlap with the image data.

The image sensor 100 may generate an image data for the inner body having n frames per second, and the additional image sensor 150 may generate an additional image data having m frames per second.

As mentioned above, the additional image data relates to an image for each wavelength band (e.g., near infrared, infrared, ultraviolet, etc.) excluding a visible light, or to an image for fluorescent material used in the fluorescence endoscopy or the fluorescence endoscopic operation, and may be a video for a specific target such as a lesion.

The image data input unit 500 may transfer the image data and the additional image data based on a setting route. That is, the image data input unit 500 may transfer the image data to the image processing unit 510 via a first transfer path, and transfer the additional image data to the CPU 520 via a second transfer path.

At this time, the image data input unit 500 may also transfer the image data to the CPU 520 via the second transfer path. The CPU 520 may transfer the additional image data slowly in comparison with the transfer speed of the image data in the first transfer path.

The image processing unit 510 may overlap the image data transferred through the first transfer path with the additional image data output from the CPU 520. Accordingly, the image data may be a background image, and the display unit (DIS) may display the superimposed additional image data on the background image.

As described above, the image data may be processed at a high speed in comparison with the additional image data. Since the image data indicates the state of the inner body, when the time delay from the generation of the image data to the display on the display unit (DIS) becomes shorter, accurate information may be provided to doctor.

Since the additional image data is the image for fluorescent material or the image for each wavelength band, the generation itself of the additional image data may be slow in comparison with the image data. For example, since the light intensity of the fluorescent material or the light intensity for each wavelength band excluding a visible light is small, in order to obtain the whole image for the additional image data, the additional image sensor 150 should be exposed to the light of the fluorescent material or the light for each wavelength band for a relatively long time.

Differently from the endoscopic system according to an embodiment of the present disclosure, when the image data and the additional image data are processed through the same path, the processing of the image data may be affected, so that the image data may not be displayed quickly and accurately through the display unit (DIS).

The endoscopic system according to an embodiment of the present disclosure may process the image data and the additional image data through a different path and may process the image data at a high speed in comparison with the additional image data so that it is possible to quickly and accurately display the image of the inner body.

The endoscope system according to an embodiment of the present disclosure may include a memory (not shown) connected with the image data input unit 500 and the CPU 520, and a memory (not shown) connected with the image processing unit 510 and the CPU 520. Each of the image data input unit 500 and the image processing unit 510 may include a standard input and output port logic such as a direct memory access (DMA) logic, a high definition multimedia interface (HDMI) logic, and DVI logic, so that it is possible to access these memory as a high speed.

This standard input output port logic may dump the image data and the additional image data to the memory, and the DMA logic of the image processing unit 510 may read the additional image data or the overlapped user interface and the additional image data from the memory. At this time, the memory may mutually transfer and receive information relating to the reading or writing of the data via a sync communication line.

As described above, the image processing unit 510 may overlap at least one of the image data, the additional image data, and the user interface.

Meanwhile, as shown in FIG. 9, the image sensor 100 may further include a first clock terminal CT1. The apparatus for transferring image data 10 may further include a clock optical fiber module 610 connected with the first clock terminal. At this time, the clock optical fiber module 610 may transfer a clock signal in a differential-mode or a single-ended mode. For example, the apparatus for transferring image data 10 may include two first optical fiber modules 200, two second optical fiber modules 300, and a single clock optical fiber module 610.

When the clock optical fiber module 610 operates in the differential mode, the clock optical fiber module 610 may be connected to the first clock terminal CT1 and the second clock terminal CT2. In addition, although not shown in FIG. 9, when the clock optical fiber module 610 operates in the single-ended mode, one terminal of the light emitting unit of the clock optical fiber module 610 may be connected with the first clock terminal CT1 and the other terminal may be connected to ground.

The image sensor 100 and the additional image sensor 150 may support a MIPI camera signal interface protocol II (MIPI CSI II) and a MIPI camera signal interface protocol III (MIPI CSI III). In this case, the MIPI CSI II and the MIPI CSI III may used for the transfer of the image data or the additional image data of a high-resolution (FHD-quality or UHD-quality).

First, a pin standard of MIPI CSI II is described with reference to FIG. 9.

In the case of MIPI CSI II, as shown in FIG. 9, the image sensor 100 and the CPU 520 may include four optical fiber modules (two first optical fiber modules 200, two second optical fiber modules 300) corresponding to a data line and a single clock optical fiber module 610 corresponding to a clock line. The clock line may transfer a clock signal which is used during the transfer or the processing of the image data.

In this case, the first optical fiber module 200 and the second optical fiber module 300 may operate in a differential mode or a single-ended mode. Since the differential mode and the single-ended mode are described above in detail, an explanation thereof is omitted.

Thus, when both of four data lines and one clock line operate in the differential mode, the first optical fiber module 200, the second optical fiber module 300, and the clock optical fiber module 610 may be connected to two terminals of the image sensor 100 respectively.

In addition, when both of four data lines and one clock line operate in the single-ended mode, the first optical fiber module 200, each terminal P of the light emitting unit of the first optical fiber module 200, the second optical fiber module 300, and the clock optical fiber module 610 may be connected to a single terminal of the image sensor 100 and the terminal N may be connected to ground.

Meanwhile, the transfer direction of the image data transferred by the first optical fiber module 200 and the second optical fiber module 300 and the transfer direction of the clock signal transferred by the clock optical fiber module 610 may be the same. That is, as shown in FIG. 9, the image data and the clock signal may be transferred toward the CPU 520 from the image sensor 100.

Meanwhile, the additional image sensor 150 may also be connected to the first additional optical fiber module 250, the second additional optical fiber module 350, and a clock additional optical fiber module 615 according to the pin standard of MIPI CSI II. The first additional optical fiber module 250, the second additional optical fiber module 350, and the clock additional optical fiber module 615 may also operate in the differential mode (see FIG. 9) or the single-ended mode (not shown).

That is, when the endoscope system according to an embodiment of the present disclosure includes the additional image sensor 150, the additional image sensor may further include a first additional clock terminal (ACT1). The apparatus for transferring image data 10 may further include the clock additional optical fiber module 615 connected to the first additional clock terminal (ACT1). In this case, the clock additional optical fiber module 615 may transfer a clock signal in the differential-mode or the single-ended mode.

For example, the endoscope system according to an embodiment of the present disclosure may include two first additional optical fiber modules 250, two second additional optical fiber modules 350, and a single clock additional optical fiber module 615.

As shown in FIG. 9, in the case of the differential-mode, the light emitting unit LT of the clock additional optical fiber module 615 may be connected to the first additional clock terminal (ACT1) and the second additional clock terminal (ACT2). In addition, although not shown in the drawing, in the case of the single-ended mode, one terminal of the light emitting unit LT of the clock additional optical fiber module 615 may be connected to the first additional clock terminal (ACT1) and the other terminal may be connected to ground.

This operation is described through the first optical fiber module 200, the second optical fiber module 300, and the clock optical fiber module 610, and an explanation thereof is omitted.

In addition, the transfer direction of the additional image data and the clock signal of the first additional optical fiber module 250, the second additional optical fiber module 350, and the clock additional optical fiber module 615 may be the same. Since this operation is similar to the above described operation of the first optical fiber module 200, the second optical fiber module 300, and the clock optical fiber module 610, a description thereof is omitted.

Next, a pin standard of MIPI CSI III different from the pin standard of MIPI CSI II is described with reference to FIG. 10.

In case of the MIPI CSI III, as shown in FIG. 10, the image sensor 100 and the CPU 520 may include four optical fiber modules (two first optical fiber modules 200, two second optical fiber modules 300) corresponding to a data line and a single synchronization confirmation optical fiber module 620 corresponding to a synchronization confirmation line.

The synchronization confirmation line may be used for transferring a synchronization confirmation signal that confirms whether synchronization is correct during the transfer and processing of the image data or a command of the CPU 520 to the image sensor 100. In the case of the MIPI CSI III, since an embedded clock is used, a separate clock optical fiber module 610 used in the MIPI CSI II may not be required. At this time, the synchronization confirmation line may also transfer a synchronization confirmation signal in the differential mode or the single-ended mode.

As described above, since both of four data lines and a single synchronization confirmation line are operable in the differential mode, the first optical fiber module 200 and the second optical fiber module 300 may be connected to two terminals of the image sensor 100 respectively, and the light reception unit LR of the synchronization confirmation optical fiber module 620 may be connected to a synchronization confirmation terminal (ST) of the image sensor 100.

Although not shown in FIG. 10, when both of four data lines and a single synchronization confirmation line operate in the single-ended mode, one terminal of the light emitting unit LT of the first optical fiber module 200 and the second optical fiber module 300 may be connected with a single terminal of the image sensor 100 respectively, and the other terminal may be connected to ground. In addition, one of two terminals of the light emitting unit LT of the synchronization confirmation optical fiber module 620 may be connected to ground, and the light reception unit LR of the synchronization confirmation optical fiber module 620 may be connected to the synchronization confirmation terminal (ST) of the image sensor 100.

As described above, the apparatus for transferring image data 10 may further include the synchronization confirmation optical fiber module 620. The synchronization confirmation optical fiber module 620 may transfer a synchronization confirmation signal in the differential mode or the single-ended mode. For example, the apparatus for transferring image data 10 may include two first optical fiber module 200, two second optical fiber module 300, and a single synchronization confirmation optical fiber module 620.

At this time, the synchronization confirmation signal may be inputted to the image sensor 100, and the image data may be output from the image sensor 100. Therefore, the transfer direction of the image data of the first optical fiber module 200 and the second optical fiber module 300 may be opposite to the transfer direction of the synchronization confirmation signal of the synchronization confirmation optical fiber module 620.

Meanwhile, when the endoscope system according to an embodiment of the present disclosure includes the additional image sensor 150, the apparatus for transferring image data 10 may further include a synchronization confirmation additional optical fiber module 625 that transfers a synchronization confirmation signal in the differential mode or the single-ended mode.

For example, thus, the endoscope system according to an embodiment of the present disclosure includes may include two first additional optical fiber module 250, two second additional optical fiber module 350, and a single synchronization confirmation additional optical fiber module 625. At this time, the synchronization confirmation additional optical fiber module 625 may be connected to an additional synchronization confirmation terminal (AST) of the additional image sensor 150.

Since the relation of the additional image sensor 150, the first additional optical fiber module 250, the second additional optical fiber module 350, and the synchronization confirmation additional optical fiber module 625 is similar to the relation of the above mentioned image sensor 100, first optical fiber module 200, second optical fiber module 300, and synchronization confirmation optical fiber module 620, an explanation thereof is omitted.

The transfer direction of the additional image data of the first additional optical fiber module 250 and the second additional optical fiber module 350 may be opposite to the transfer direction of the synchronization confirmation signal of the synchronization confirmation additional optical fiber module 625. In this case, since it is similar to the relation of the transfer direction of the image data and the synchronization confirmation signal of the synchronization confirmation optical fiber module 620, an explanation thereof is omitted.

On the other hand, the endoscope system according to an embodiment of the present disclosure may include the apparatus for transferring image data 10 that can implement both the MIPI CSI II and the MIPI CSI III.

To this end, the apparatus for transferring image data 10 may include the first optical fiber module 200, the second optical fiber module 300, a first transfer direction optical fiber module (OF_D1), and a second transfer direction optical fiber module (OF_D2).

At this time, the signal transfer direction of the first transfer direction optical fiber module (OF_D1) may be opposite to the signal transfer direction of the second transfer direction optical fiber module (OF_D2), and may be identical to the transfer direction of the image data of the first optical fiber module 200 and the second optical fiber module 300.

For example, as shown in FIG. 11 and FIG. 12, the apparatus for transferring image data 10 may include two first optical fiber modules 200, two second optical fiber modules 300, a single first transfer direction optical fiber module (OF_D1), and a single second transfer direction optical fiber module (OF_D2).

As this time, as shown in FIG. 11, when the apparatus for transferring image data 10 satisfies the MIPI CSI II, the apparatus for transferring image data 10 may further include a dummy optical fiber module 630 that can transfer a signal in the opposite direction of the transfer direction of the image data and the clock signal.

That is, the first transfer direction optical fiber module (OF_D1) may be the clock optical fiber module 610 and the second transfer direction optical fiber module (OF_D2) may be the dummy optical fiber module 630. This dummy optical fiber module 630 may be used as an extra optical fiber module for transferring various signals or data transferred from the CPU 520 to the image sensor 100.

In addition, when the apparatus for transferring image data 10 further includes the additional image sensor 150, it may further include an additional dummy optical fiber module 635 which can transfer a signal in the opposite direction of the transfer direction of the additional image data and the clock signal.

Meanwhile, as shown in FIG. 12, when the apparatus for transferring image data 10 satisfies the MIPI CSI III, the apparatus for transferring image data 10 may further include the dummy optical fiber module 630 in addition to the first optical fiber module 200, the second optical fiber module 300, and the synchronization confirmation optical fiber module 620.

At this time, the dummy optical fiber module 630 may transfer a signal in the same direction as the transfer direction of the image data. That is, the first transfer direction optical fiber module (OF_D1) may be the dummy optical fiber module 630, and the second transfer direction optical fiber module (OF_D2) may be the synchronization confirmation optical fiber module 620.

When one of the first optical fiber module 200 and the second optical fiber module 300 is an abnormal optical fiber module which is not able to transfer the image data, the dummy optical fiber module 630 which is the first transfer direction optical fiber module (OF_D1) may transfer the image data instead of the abnormal optical fiber module. Accordingly, the operation stability of the endoscope system can be improved.

When the apparatus for transferring image data 10 includes the additional image sensor 150, and the additional image sensor 150 satisfies the MIPI CSI III, it may further include the additional dummy optical fiber module 635 which can transfer a signal in the same direction as the transfer direction of the additional image data.

Similarly to the above explanation, when one of the first additional optical fiber module 250 and the second additional optical fiber module 350 is an abnormal additional optical fiber module which is not able to transfer the image data, the additional dummy optical fiber module 635 may transfer the image data instead of the abnormal additional optical fiber module.

The above mentioned MIPI CSI II standard and MIPI CSI III standard are just an example, and the embodiment of the present disclosure is not limited to these standards.

Meanwhile, as shown in FIG. 8, the endoscope system according to an embodiment of the present disclosure may further include a control optical fiber module 640 and an input optical fiber module 650. First, the control optical fiber module 640 is described.

The control optical fiber module 640 may be used for communication among the CPU 520, a focusing unit 530, the image sensor 100, and the additional image sensor 150, and thus, the focusing unit 530, the image sensor 100, and the additional image sensor 150 may be controlled by the CPU 520.

The focusing unit 530 may drive a focusing lens under the control of the CPU 520 to implement an auto-focusing of the image sensor 100 or the additional image sensor 150. In addition, the image sensor 100 and the additional image sensor 150 may be initialized in response to a control signal of the CPU 520. These auto-focusing and initializing are just an example of the control by the CPU 520, and various controls for the image sensor 100, the additional image sensor 150, and the focusing unit 530 may be accomplished by the CPU 520.

The endoscope system according to an embodiment of the present disclosure may include a communication chip 540 for performing a communication between the CPU 520 and the focusing unit 530, a communication between the CPU 520 and the image sensor 100, a communication between the CPU 520 and the additional image sensor 150. The communications chip 540 may support a specific communication standard such as I²C, but it is not limited to the I²C communication standard.

At this time, the communication chip 540 may be embedded in the focusing unit 530, the image sensor 100, and the additional image sensor 150. The control optical fiber module 640 may be connected with every communication chip 540 used in the communication process with the CPU 520.

FIG. 8 illustrates that a single control optical fiber module 640 is connected to each communication chip 540, but it is illustrated for the convenience of explanation and it is not limited thereto.

For example, as shown in FIG. 13, a plurality of communication chips 540 may communicate with the CPU 520 via a communication bus. A single control optical fiber module 640 may be connected to a single communication bus. Two communication bus lines may be used for transferring and receiving to and from the CPU 520. That is, one communication bus line may be used for the reception of the control signal outputted from the CPU 520, and another communication bus line may be used for transferring operation information to the CPU 520.

The operation information may be information that the CPU 520 receives from the focusing unit 530, the image sensor 100 and the additional image sensor 150 so as to accomplish a control. For example, the operation information may be information related to the current state of the focusing unit 530, the image sensor 100, and the additional image sensor 150, but it is not limited thereto.

In addition, although not shown in FIG. 13, a clock bus line for transferring a clock signal from the CPU 520 to the focusing unit 530, the image sensor 100, and the additional image sensor 150 may be added, and the clock bus line may also be connected to the control optical fiber module.

Thus, in the case of performing the bus communication, the number of control optical fiber module 640 may be reduced. That is, as shown in FIG. 13, when using the communication bus, two control optical fiber modules 640 may be necessary for a plurality of communication chips 540. On the other hand, when the communication bus is not used, each communication chip 540 should be connected to the control optical fiber module 640 so that the number of the control optical fiber module 640 may be increased.

That is, the image sensor 100 and the CPU 520 may perform a communication via the communication bus, and the communication bus may include a transfer bus line and a reception bus line. In this case, each of the transfer bus line and the reception bus line may be connected to the control optical fiber module 640.

In addition, the additional image sensor 150 and the focusing unit 150 may also communicate with the CPU 520 via the communication bus.

Next, the input optical fiber module 650 is described.

As shown in FIG. 8, the endoscope system according to an embodiment of the present disclosure may include an input unit 550. The input unit 550 may generate an input signal for selecting the up, down, left, and right movements of the image generation unit 20, a white balance for the image data or the additional image data, and a menu selection according to a user's handling. According to such an input signal, the CPU 520 may control the endoscope system.

For convenience of explanation, a driving unit for the up, down, left, and right movements of the image generation unit 20 is not shown in FIG. 8.

Such an input signal may be transferred to the CPU 520 via the input optical fiber module 650 connected to the input unit 550, and six input optical fiber modules 650 for each of the up, down, left, and right movements of the image generation unit 20, the adjustment of the white balance for the image data or the additional image data, and the menu selection may be included, but the number of the input optical fiber module 650 may be increased or decreased. The input unit 550 may include a general purpose input/output (GPIO) port, but it is not limited thereto.

In the case of the endoscope system of FIG. 8, the optical fiber module and the control optical fiber module 640 connected to the input unit 550 and the communication chip 540 may be connected to the image data input unit 500 so that the number of optical fiber module may be increased.

For example, as mentioned above, when the input unit 550 is connected to six input optical fiber modules 650, and a communication bus for a plurality of communication chip 540 is connected to two control optical fiber modules 640, eight optical fiber modules may be more required in addition to the optical fiber module connected to the image sensor 100 or the additional image sensor 150.

In this case, the number of optical fiber surrounded by the protection unit OFP may also be increased so that the thickness of the apparatus for transferring image data 10 may be excessively increased.

As shown in FIG. 14, the endoscope system according to an embodiment of the present disclosure may further include a micro control unit (MCU) 560 to reduce the number of optical fiber module.

The endoscope system according to an embodiment of the present disclosure may further include the input unit 550 which can be handled by a user, the MCU 560 which encodes an input signal of the input unit 550, and a third optical fiber module 660 which is connected to the MCU 560 and which transfers the input signal encoded by the MCU 560. In this case, the number of the third optical fiber module 660 for transferring the encoded input signal may be smaller than the number of input pins of the MCU 560 which receives the input signal from the input unit 550.

For example, as shown in FIG. 15, since the input unit 550 may generate an input signal for the up/down/left/right, the white balance, and the menu selection, the MCU 560 may be provided with six input pins for these input signals.

The MCU 560 may receive these input signals in parallel to encode and output to an output terminal, and the third optical fiber module 660 may be connected to the output terminal. Such a third optical fiber module 660 may communicate with the CPU 520 via the image data input unit 500 or may be connected directly to the CPU 520.

Differently from the embodiment of the present disclosure, if there is no MCU 560, as described above, the input unit 550 should be connected with six input optical fiber modules 650, but in the embodiment of the present disclosure, the number of the third optical fiber module 660 which transfers the encoded input signal may be smaller than six input optical fiber modules 650 due to the MCU 560.

Meanwhile, as shown in FIG. 14, and FIG. 15, the endoscope system according to an embodiment of the present disclosure may further include the additional image sensor 150, the MCU 560, and the third optical fiber module 660.

The additional image sensor 150 may generate additional image data by sensing a light having a wavelength different from the wavelength of light sensed by the image sensor 100.

The MCU 560 may input and output a control signal and operation information for the image sensor 100 and the additional image sensor 150. That is, the MCU 560 may output the control signal to the image sensor 100 and the additional image sensor 150, and receive the operation information from the image sensor 100 and the additional image sensor 150.

The third optical fiber module 660 may be connected to the MCU 560 to transfer and receive the control signal and the operation information to and from the CPU 520. That is, the MCU 560 may receive the control signal from the CPU 520 via one optical fiber module 660, and may transfer the operation information to the CPU 520 via another optical fiber module.

In this case, the number of the third optical fiber module 660 may be smaller than or equal to the number of pins of the MCU 560 for inputting and outputting the control signal and the operation information.

Since the control signal and the operation information are described above in detail, an explanation thereof is omitted.

The MCU 560 may be connected with one third optical fiber module 660 and may decode the control signal from the CPU 520 to transfer to the communication bus.

In addition, the MCU 560 may receive the operation information relating to at least one of the image sensor 100, the additional image sensor 150, and the focusing unit 530 via the communication bus and may encode the received operation information to transfer to the CPU 520 via another third optical fiber module 660.

The encoding and decoding of the MCU 560 are just an example of the occurrence in the communication process between the MCU (560) and the CPU 520, and the operation of the MCU 560 in not limited thereto.

As explained above, when the image sensor 100 and the additional image sensor 150 communicate with the CPU 520 via the communication bus, the MCU 560 may have two terminals for the transfer and reception of the control signal and the operation information, and the two terminals may be connected to the communication bus.

In addition, the MCU 560 may transfer and receive the control signal and the operation information via two third optical fiber modules 660. Accordingly, the number of the third optical fiber module 660 may be the same as the number of pins of the MCU 560 for inputting and outputting the control signal and the operation information of the image sensor 100 and the additional image sensor 150.

When a communication with a plurality of communication chips 540 is achieved without the communication bus, the MCU 560 should be provided with two terminals per one communication chip 540 for transferring and receiving so that the number of the third optical fiber module 660 may be smaller than the number of pins of the MCU 560 for outputting the control signal of the image sensor 100 and the additional image sensor 150.

Meanwhile, as shown in FIG. 8 and FIG. 14, the protection unit OFP of the apparatus for transferring image data 10 may be implemented of material that can withstand the autoclave for the disinfection of a medical device. Since the endoscope system of the present disclosure is also a medical device, autoclave may be accomplished. Autoclave may be accomplished for 20 minutes at steam atmosphere of 20 atm 120 degrees, and an optical fiber may be melted at a temperature lower than 120 degrees.

The protection unit OFP may cover the optical fiber to protect the optical fiber from the autoclave process. Since disinfection is performed by using a steam during the autoclave, the temperature of the steam is high, but heat capacity is small, so that the protection unit OFP in the embodiment of the present disclosure may include a heat shield rubber to protect the optical fiber.

As described above, the protection unit OFP may protect the optical fibers of various optical fiber modules such as the first to the third optical fiber modules 660, the first and the second additional optical fiber module 350, the control optical fiber module 640, and the input optical fiber module 650.

As shown in FIG. 8 and FIG. 14, the endoscope system according to an embodiment of the present disclosure may further include a monitoring unit 570. The monitoring unit 570 may monitor at least one of the image data input unit 500, the CPU 520, and the image processing unit 510 in real time to perform a reset of the at least one according to the state value of the at least one.

Since the endoscope system is used for medical use, the processing of the image data and the additional image data should always be accomplished stably. For example, when doctor is not able to see the image of the inner body during a surgical procedure, the surgical procedure may not be accomplished smoothly.

Thus, the monitoring unit 570 may perform real-time monitoring of at least one of the image data input unit 500, the image processing unit 510, and the CPU 520 that perform the processing of the image data, the additional image data, and the user interface.

For example, the monitoring unit 570 may receive the state value of at least one of the image data input unit 500, the image processing unit 510, and the CPU 520 every 1 ms, and a cycle of receiving the state value may be greater or less than 1 ms**.

The monitoring unit 570 may reduce or minimize the time of the abnormal image processing or the user interface processing by resetting a corresponding element of the state value indicating abnormality or error.

Since such a monitoring unit 570 performs a simple function in comparison with the CPU 520, it may be implemented in the form of micro control unit or firmware, but it is not limited thereto.

As above described, the apparatus for transferring image data 10 and the endoscope system according to an embodiment of the present disclosure may include an optical fiber module instead of a coaxial cable, so that it is possible to provide the apparatus for transferring image data 10 having a diameter smaller than that of the coaxial cable.

Accordingly, the apparatus for transferring image data 10 and the endoscope system according to an embodiment of the present disclosure may overcome the bandwidth limit of the coaxial cable so that it is possible to transfer the image data or the additional image data of high resolution or ultra-high-resolution.

Furthermore, the encoding, the serializing, the deserializing, and the decoding may not be performed through the optical fiber module so that it is possible to transfer the image data and the additional image data more fast.

As above described, the apparatus for transferring image data according to an embodiment of the present disclosure and the endoscope system including the same may include an optical fiber module to overcome the bandwidth limit.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. An apparatus for transferring image data, the apparatus comprising:
   an image sensor configured to generate an image data, and to comprise a first image terminal and a second image terminal for transferring at least a portion of the image data;
   a first optical fiber module and a second optical fiber module connected to the first image terminal and the second image terminal respectively;
   an additional image sensor configured to generate an additional image data by sensing a light having a wavelength different from a wavelength of light sensed by the image sensor, and to include a first additional image terminal and a second additional terminal for transferring at least a portion of the additional image data; and
   a first additional optical fiber module and a second additional optical fiber module which are connected to the first additional image terminal and the second additional terminal respectively,
   wherein at least a portion of the image data is transferred through the first optical fiber module and the second optical fiber module without a serialization process for the image data.

2. The apparatus of claim 1, wherein the first optical fiber module is connected to a third image terminal together with the first image terminal,
   the second optical fiber module is connected to a fourth image terminal together with the second image terminal, and
   the first optical fiber module and the second optical fiber module transfer the image data in a differential mode.

3. The apparatus of claim 1, wherein the first optical fiber module and the second optical fiber module transfer the image data in a single-ended mode.

4. The apparatus of claim 1, wherein the first optical fiber module and the second optical fiber module are directly connected to the first image terminal and the second image terminal, or connected to the first image terminal and the second image terminal through a connector.

5. The apparatus of claim 1, wherein the first additional optical fiber module is connected to a third additional image terminal together with the first additional image terminal, the second additional optical fiber module is connected with a fourth additional image terminal together with the second additional image terminal, and the first additional optical fiber module and the second additional optical fiber module transfer the additional image data in a differential mode.

6. The apparatus of claim 1, wherein the first additional optical fiber module and the second additional optical fiber module transfer the additional image data in a single-ended mode.

7. The apparatus of claim 1, wherein at least a portion of the additional image data is transferred through the first additional optical fiber module and the second additional optical fiber module without a serialization process for the additional image data.

8. An endoscope system comprising:
   an apparatus for transferring image data including an image sensor which generates image data and which includes a first image terminal and a second image terminal for transferring at least a portion of the image data, a first optical fiber module and a second optical fiber module which are connected with the first image terminal and the second image terminal respectively, an additional image sensor configured to generate an additional image data by sensing a light having a wavelength different from a wavelength of light sensed by the image sensor, and to include a first additional image terminal and a second additional terminal for transferring at least a portion of the additional image data, and a first additional optical fiber module and a second additional optical fiber module which are connected to the first additional image terminal and the second additional terminal respectively;
an image data input unit configured to be connected with the apparatus for transferring image data and to transfer the image data output through the apparatus for transferring image data via a set path; and
an image processing unit configured to perform an image processing for the image data transferred from the image data input unit under control of CPU,
wherein at least a portion of the image data is transferred through the first optical fiber module and the second optical fiber module without a serialization process for the image data.

9. The endoscope system of claim 8, wherein the CPU processes an user interface for the image data, and the image processing unit overlaps the user interface with the image data.

10. The endoscope system of claim 8, wherein the first optical fiber module and the second optical fiber module transfer the image data in a differential mode or a single-ended mode.

11. The endoscope system of claim 8, wherein the first optical fiber module and the second optical fiber module are directly connected to the first image terminal and the second image terminal, or connected to the first image terminal and the second image terminal through a connector.

12. The endoscope system of claim 8, wherein the image data input unit receives the additional image data together with the image data and transfers the additional image data to the CPU, and transfers the image data to the image processing unit, and the image processing unit receives the additional image data from the CPU to overlap with the image data.

13. The endoscope system of claim 8, wherein the image sensor further comprises a first clock terminal, and the apparatus for transferring image data further comprises a clock optical fiber module connected with the first clock terminal,
wherein the clock optical fiber module transfers a clock signal in a differential-mode or a single-ended mode.

14. The endoscope system of claim 13, wherein a transfer direction of the image data which the first optical fiber module and the second optical fiber module transfer is identical with a transfer direction of the clock signal which the clock optical fiber module transfers.

15. The endoscope system of claim 14, wherein the apparatus for transferring image data further comprises a dummy optical fiber module which is able to transfer a signal in an opposite direction of the transfer direction of the image data and the clock signal.

16. The endoscope system of claim 8, wherein the additional image sensor further comprises a first additional clock terminal, and the apparatus for transferring image data further comprises a clock additional optical fiber module connected to the first additional clock terminal,
wherein the clock additional optical fiber module transfers a clock signal in the differential-mode or the single-ended mode.

17. The endoscope system of claim 16, wherein transfer directions of the additional image data and the clock signal of the first additional optical fiber module, the second additional optical fiber module, and the clock additional optical fiber module are identical.

18. The endoscope system of claim 17, further comprises an additional dummy optical fiber module which is able to transfer a signal in the opposite direction of the transfer direction of the additional image data and the clock signal.

19. The endoscope system of claim 10, wherein the apparatus for transferring image data further comprises a synchronization confirmation optical fiber module, wherein the synchronization confirmation optical fiber module transfers a synchronization confirmation signal in the differential-mode or the single-ended mode.

20. The endoscope system of claim 19, wherein the transfer direction of the image data of the first optical fiber module and the second optical fiber module is opposite to the transfer direction of the synchronization confirmation signal of the synchronization confirmation optical fiber module.

21. The endoscope system of claim 20, further comprising a dummy optical fiber module configured to transfer a signal in the same direction as the transfer direction of the image data.

22. The endoscope system of claim 21, wherein, when one of the first optical fiber module and the second optical fiber module is an abnormal optical fiber module which is not able to transfer the image data, the dummy optical fiber module transfers the image data instead of the abnormal optical fiber module.

23. The endoscope system of claim 8, wherein the apparatus for transferring image data further comprises a synchronization confirmation additional optical fiber module, wherein synchronization confirmation additional optical fiber module transfers a synchronization confirmation signal in the differential mode or the single-ended mode.

24. The endoscope system of claim 23, wherein the transfer direction of the additional image data of the first additional optical fiber module and the second additional optical fiber module is opposite to the transfer direction of the synchronization confirmation signal of the synchronization confirmation additional optical fiber module.

25. The endoscope system of claim 24, further comprising an additional dummy optical fiber module configured to transfer a signal in the same direction as the transfer direction of the additional image data.

26. The endoscope system of claim 25, wherein, when one of the first additional optical fiber module and the second additional optical fiber module is an abnormal additional optical fiber module which is not able to transfer the image data, the additional dummy optical fiber module transfers the image data instead of the abnormal additional optical fiber module.

27. The endoscope system of claim 8, further comprising an input unit which is able to be handled by a user, a micro control unit (MCU) configured to encode an input signal of the input unit, and a third optical fiber module configured to be connected to the MCU and to transfer the input signal encoded by the MCU.

28. The endoscope system of claim 8, wherein the apparatus for transferring image data further comprises a protection unit configured to protect each optical fiber of the first optical fiber module and the second optical fiber module,
wherein the protection unit is implemented of material that is able to withstand autoclave for disinfection of a medical device.

29. The endoscope system of claim 8, further comprising a monitoring unit configured to monitor at least one of the image data input unit, the CPU, and the image processing unit in real time to perform a reset of the at least one of the image data input unit, the CPU, and the image processing unit according to a state value of the at least one of the image data input unit, the CPU, and the image processing unit.

30. The endoscope system of claim 8, wherein the image sensor and the CPU communicate via a communication bus,
wherein the communication bus comprises a transfer bus line and a receive bus line,
wherein the transfer bus line and the receive bus line are connected with a control optical fiber module respectively.

* * * * *